US009078872B2

(12) United States Patent
Erfurt et al.

(10) Patent No.: US 9,078,872 B2
(45) Date of Patent: Jul. 14, 2015

(54) ANTIOXIDANT COMPOSITION

(71) Applicant: Symrise AG, Holzminden (DE)

(72) Inventors: Harry Erfurt, Ulsar (DE); René Schuld, Wedel (DE); Melanie Stürtz, Höxter (DE); Christian Wintermeyer, Höxter (DE); Hans-Jürgen Niemeyer, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/248,883

(22) Filed: Apr. 9, 2014

(65) Prior Publication Data

US 2014/0309294 A1    Oct. 16, 2014

(30) Foreign Application Priority Data

Apr. 14, 2013  (EP) .................................. 13163647

(51) Int. Cl.
| A61K 31/353 | (2006.01) |
| A61K 31/192 | (2006.01) |
| A61K 8/36 | (2006.01) |
| A61K 8/49 | (2006.01) |
| A23L 3/3517 | (2006.01) |
| A23L 3/3508 | (2006.01) |
| A23L 1/30 | (2006.01) |
| A61Q 19/00 | (2006.01) |
| A61K 31/352 | (2006.01) |

(52) U.S. Cl.
CPC .............. *A61K 31/353* (2013.01); *A23L 1/3002* (2013.01); *A23L 3/3508* (2013.01); *A23L 3/3517* (2013.01); *A61K 8/36* (2013.01); *A61K 8/498* (2013.01); *A61K 31/192* (2013.01); *A61K 31/352* (2013.01); *A61Q 19/00* (2013.01)

(58) Field of Classification Search
USPC ......................... 514/456; 426/321, 544, 546
See application file for complete search history.

(56) References Cited

FOREIGN PATENT DOCUMENTS

| DE | 10 2011 052708 A1 | 2/2013 |
| EP | 2550872 A1 | 1/2013 |
| WO | 2005/070380 A1 | 8/2005 |
| WO | 2013/016257 A1 | 1/2013 |

OTHER PUBLICATIONS

Li et al; "Comparison of antioxidant capacity and phenolic compounds of berries, chokeberry and seabuckthorn," Cent. Eur. J. Biol., vol. 4, No. 4, 2009, pp. 499-506.

*Primary Examiner* — Kristin Vajda
(74) *Attorney, Agent, or Firm* — Dilworth & Barrese, LLP

(57) ABSTRACT

Suggested is an antioxidant composition, comprising
(a) caffeic acid,
(b) sinapinic acid and, optionally,
(c) polyphenols,
with the proviso that components (a) and (b) are present in a weight ratio of about 85:15 to about 98:2.

18 Claims, 1 Drawing Sheet

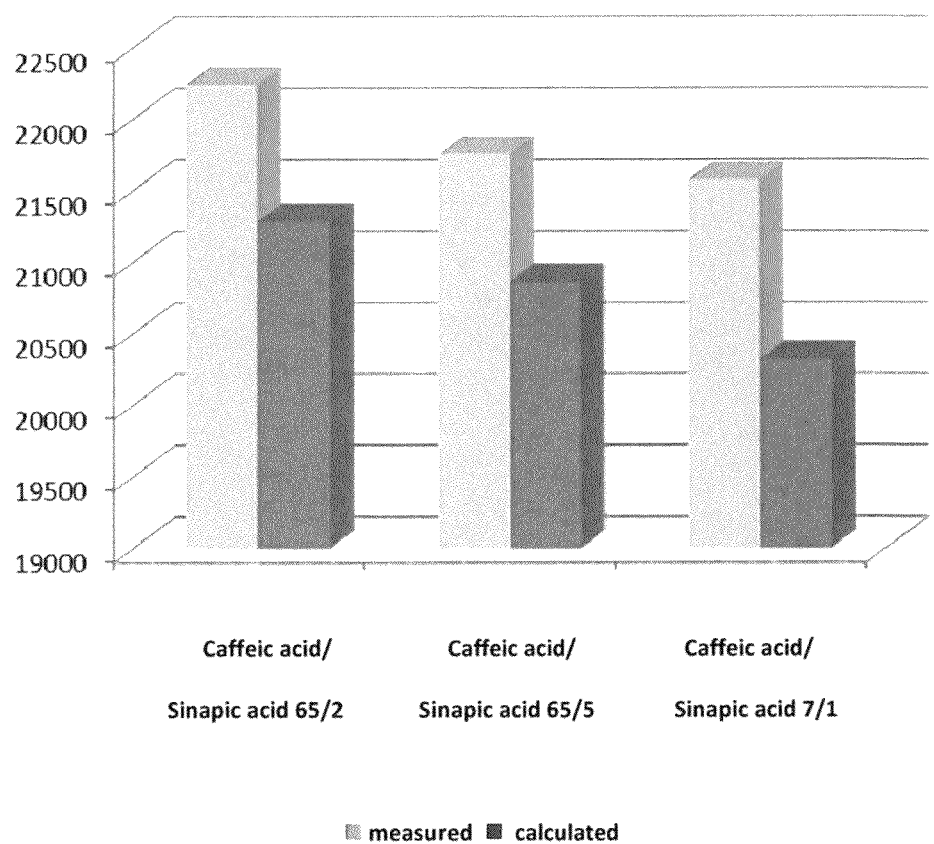
Synergistic increase of the antioxidant effect when comparing the calculated and measuresd ORAC values

ANTIOXIDANT COMPOSITION

FIELD OF THE INVENTION

The invention is in the field of antioxidants and relates to compositions comprising a synergistic combination of particular hydroxycinnamic acids, optionally in combination with polyphenols, extracts of plants and fruits containing them, a method of production of said extracts, specifically based on sour cherries, and uses of the synergistic combination of antioxidants in the most diverse fields.

PRIOR ART

Oxidative cell damage, particularly damage to the genetic material, is one of the most dangerous environmental influences, constituting a particular danger to the human organism. High-energy radiation, particularly in combination with oxygen, creates highly reactive radicals which are also referred to as "reactive oxygen species—ROS", which are, for example, capable of changing the DNA such that thymine is oxidized to form thymine glycol, or guanine is oxidized to form 8-oxoguanine (8-OxoG). Specifically the latter one is an aggressive mutagenic substance, because during the replication opposite an 8-OxoG both the normal cytosine nucleotide and, preferably, an adenine nucleotide may be incorporated. Incorrect transversion is one of the causes of cell defects and, eventually, of cancer. Oxidative stress triggered by ROS will also lead to accelerated skin aging, which is regularly observed when people excessively expose themselves to UV radiation (for example, in tanning centers).

It is therefore obvious that there is considerable interest in protecting the human organism against such oxidative damage. For example, this may be performed by administering substances which quench radicals, whereby these so-called antioxidants can be ingested orally—either together with the food or separately as dietary supplements—or be topically applied, for example, in cosmetic products that are brought in contact with the skin.

Various natural substances have proven their effectiveness as antioxidants. Besides vitamin C (ascorbic acid) the most well-known include the different carotene derivatives (e.g. beta carotene, lycopene, luteine) and, particularly, vitamin E and its derivatives (tocopherol, tocopheryl acetate and tocopheryl palmitate). Another important group is constituted of the polyphenols, specifically the anthocyanins and isoflavones, which are contained, for example, in a variety of red fruits. It is known, however, that juices and extracts of said fruits also contain low amounts of phenolic acids and hydroxycinnamic acids, particularly chlorogenic acid, but with regard to the influence on the antioxidant potential of these anthocyanin-rich extracts these associated materials have not yet received much attention.

There is continued interest in the market to improve both the potential and the range of efficiency of such natural antioxidants, either by achieving a higher performance with the same amounts or, vice versa, by achieving the same performance with lower amounts.

It has therefore been the object of the present invention to improve existing polyphenol-containing compositions, particularly, extracts with a high content of anthocyanins or anthocyanidins such that they show an increased antioxidant performance.

DESCRIPTION OF THE INVENTION

In a first form of embodiment the subject matter of the invention concerns an antioxidant composition, comprising (a) caffeic acid,
(b) sinapinic acid and, optionally,
(c) polyphenols, with the proviso that components (a) and (b) are present in a weight ratio of about 85:15 to 98:2 and, particularly, about 87:13 to 97:3. Preferably, components (a+b) and (c) are contained in a weight ratio of about 5:95 to about 1:99 and, more preferably, about 4:96 to about 2:98.

In a second form of embodiment an extract is claimed, comprising (a) caffeic acid,
(b) sinapinic acid and, optionally,
(c) polyphenols, with the proviso that components (a) and (b) are present in a weight ratio of about 85:15 to 98:2, preferably, of about 87:13 to 97:3.

Surprisingly it was found that among the hydroxycinnamic acids contained in the anthocyanin extracts particularly caffeic acid and sinapinic acid show a strong synergy with respect to their antioxidant properties as was shown in an ORAC (Oxygen Radical Absorbance Capacity) test. In addition, these positive properties are already verifiable in very small amounts of use of both substances, and intensify when in contact with polyphenols, particularly anthocyanins.

BRIEF DESCRIPTION OF THE DRAWING

The present invention will be described in greater detail with reference to the accompanying drawing which is a graph of measured and calculated synergistic increase of antioxidant effect.

DESCRIPTION OF THE PREFERRED EMBODIMENTS

The compositions can be used individually or in the form of extracts obtainable from plants or fruits according to a particular method. Both the compositions and the extracts are extremely suitable for use as additives for food products, dietary supplements, but also in the production of pharmaceutical compositions aimed at an improved protection of cells against oxidative damage, for example, by UV radiation. In addition to these uses in which the products are orally ingested also a topical use is considered, in which the compositions or extracts are incorporated into cosmetic compositions, specifically, into skin care, hair care, and sunscreen products.

Hydroxycinnamic Acids

Caffeic acid (3,4-dihydroxycinnamic acid) and sinapinic acid (3-(4-hydroxy-3,5-dimethoxy-phenyl)-prop-2-enoic acid)

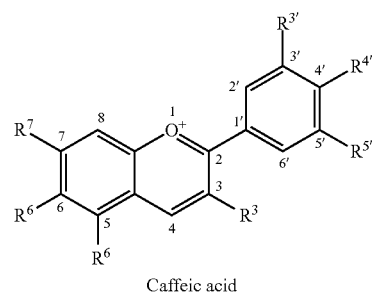

Caffeic acid

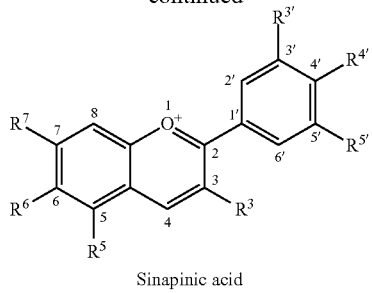

Sinapinic acid belong to the hydroxycinnamic acids contained in many plants and fruits, specifically in berries.

Polyphenols

The polyphenols forming optional component (c) are preferably anthocyanins or anthocyanidins.

Anthocyanins are water-soluble chymochrome pigments of the general formula (I)

(I)

and which are only found in the cell sap of land plants, but not in animals, microorganisms or aquatic plants. Anthocyanins are present in nearly all higher plants, mostly in the blossoms and fruits, but also in the leaves and roots. They are particularly present in the peripherical cell layers such as in the epidermic cells of the respective plant parts. The amounts found there are relatively large: for example, a kilogram of blackberries contains about 1.15 grams of anthocyanins, and a kilogram of peel of red and black pulses yields up to 20 grams. Table A provides an overview of the most significant anthocyanins:

ferred within the meaning of the invention are glucosides, rutinosides, rhamnosides, galactosides and arabinosides of cyanidin, delphinidin, peonidin and petunidin, as contained in particularly high concentrations, for example, in sour cherries. Accordingly, the corresponding extracts are also particularly preferred.

In addition to the anthocyanins or anthocyanidins, the compositions or extracts may, however, advantageously, also contain flavones or flavone glycosides such as, for example, catechins (e.g., catechin, epicatechin, epigallocatechin gallate (EGCG), gallocatechin, gallocatechin-3-gallate, epicatechin gallate), iso-catechin or prunetin.

Extracts

The extracts of the invention are preferably characterized in that they contain (a) about 150 to 1.000 ppm, preferably, about 300 to 900 ppm and particularly about 550 to 750 ppm caffeic acid,
(b) 10 to 50 ppm, preferably, about 12 to 40 ppm and particularly about 15 to 25 ppm sinapinic acid, and
(c) 10 to 60% by weight, preferably, about 20 to 50% by weight, and particularly about 25 to 45% by weight polyphenols, and that they are essentially filled up to 100% by weight with solvents, wherein the selection rule applies again, according to which components (a) and (b) are present in a weight ratio of about 85:15 to 98:2, preferably, about 87:13 to 97:3. In addition, the extracts have a total content of hydroxycinnamic acids of about 0.5 to about 3% by weight, preferably, of about 0.7 to 1.5. Further components are, for example, sugars in insubordinate amounts.

The extracts, particularly the extracts on the basis of sour cherries, are further characterized in that they show the following parameters with the proviso that parameters (a) to (e) can be met all together or individually or in an arbitrary combination, thus expressly disclosing all possible iterations, also with regard to the combination of preferred ranges within different parameters:

(a) an ORAC value of above 5,000, preferably above 6,000 and particularly above 10,000; and/or
(b) a polyphenol content of above 40% by weight, preferably above 45% by weight and particularly above 50% by weight; and/or
(c) a anthocyanin content of about 6 to about 25% by weight, preferably of about 15 to about 20% by weight and particularly about 16 to 18% by weight; and/or

TABLE A

Anthocyanins

| Anthocyanidins | Basic structure | $R_{3'}$ | $R_{4'}$ | $R_{5'}$ | $R_3$ | $R_5$ | $R_6$ | $R_7$ |
|---|---|---|---|---|---|---|---|---|
| Aurantinidin | | —H | —OH | —H | —OH | —OH | —OH | —OH |
| Cyanidin | | —OH | —OH | —H | —OH | —OH | —H | —OH |
| Delphinidin | | —OH | —OH | —OH | —OH | —OH | —H | —OH |
| Europinidin | | —OCH$_3$ | —OH | —OH | —OH | —OCH$_3$ | —H | —OH |
| Luteolinidin | | —OH | —OH | —H | —H | —OH | —H | —OH |
| Pelargonidin | | —H | —OH | —H | —OH | —OH | —H | —OH |
| Malvidin | | —OCH$_3$ | —OH | —OCH$_3$ | —OH | —OH | —H | —OH |
| Peonidin | | —OCH$_3$ | —OH | —H | —OH | —OH | —H | —OH |
| Petunidin | | —OH | —OH | —OCH$_3$ | —OH | —OH | —H | —OH |
| Rosinidin | | —OCH$_3$ | —OH | —H | —OH | —OH | —H | —OCH$_3$ |

The glycosides of cyanidin, delphinidin, malvidin, pelargonidin, peonidin and petunidin are most often found in nature and are referred to as anthocyanins. Particularly pre- (d) an ash content of less than 3% by weight, preferably less than 2% by weight and particularly of about 0.5 to about 1% by weight; and/or (e) a sugar content of less than 0.25% by weight, preferably less than 0.1% by weight and particularly 0% by weight.

The extracts are obtained on the basis of plants or fruits selected from the group consisting of Açai (*Euterpe olerocea*);
Aronia (e.g. *Aronia arbutifolia, Aronia melanocarpa; Aronia prunifolia*);
Black currant and red currant (e.g. *Ribes rubrum, Ribes spciotum, Ribes alpinum, Ribes schlechtendalil, Ribes multiflorum, Ribes petraeum, Ribes trite, Ribes nigrum*);
Black berries (*Rubus* sp.);
Black carrots (*Daucus carota*);
Black tomatoes (*Solanum lycopersicum*);
Blood oranges (*Citrus sinensis*);
Blueberries (*Vaccinium corymbosum, Vaccinium angustifolium*);
Black haw (*Prunus spinosa*);
Bilberries (*Vaccinium ulginosum*);
Cloudberries (*Rubus chamoemorus*);
Lingonberries (e.g. *Vaccinium oxycoccos, Vaccinium microcarpus, Vaccinium macrocarpus, Vaccinium erythrocarpus*);
Black crowberries (e.g. *Empetrum nigrum, Empetrum eamesii, Empetrum rumbrum, Empetrum hermophroditum*);
Elderberries (e.g. *Sambucus nigro, Sambucus racemosa*);
Hibiscus (*Hibiscus sabdariffa*, Roselle);
Cowberries (e.g. *Vaccinium vitus idaea*);
Magellan barberries ("Calafate", *Berberis microphylla, Berberis buxifolia*);
Maqui berries (e.g. *Aristotelia chilensis*);
Mountain huckleberries (*Vaccinium membranaceum*);
Plums and damsons (*Prunus domestica*);
Raspberries (*Rubus idaeus, Rubus occidentalis*);
Red gooseberries (*Ribes uva-crispa, Ribes grossularia*);
Red grapes (*Vitis vinifera, Vitis labrusca, Vitis riparia, Vitis rotundifolia*);
Rowanberries (*Sorbus oucuparia*);
Sour cherries (e.g. *Prunus avium, Prunus cerasus*);
Strawberries (*Fragaria ananassa*);
Sweet cherries (*Prunus avium*);
Tay berries (*Rubus* X).

It is furthermore advantageous if the disaccharide content of the compositions is less than 2% by weight, particularly about 0.1 to 1.5% by weight. Further it is typical that preferred compositions have a significant potassium content, particularly of about 10 to about 5.000, preferably about 100 to about 2.500 and particularly preferably about 200 to about 1.000 ppm.

A further subject matter of the invention concerns a method of production of a corresponding extract, which comprises caffeic and sinapinic acids in the synergistic weight ratio, wherein
(i) a juice or an extract is obtained from the plants or fruits, which is then acidified,
(ii) the acidified product is passed over an adsorber column which contains as adsorption means a macroporous, crosslinked, non-functionalised polystyrene resin,
(iii) the mixture comprising components (a), (b) and (c) is desorbed using aqueous, preferably, acidified alcohol and, finally,
(iv) the eluate is dried.

The juice can be preferably obtained from the fruits by squeezing. For example, if *hibiscus* leaves are used, alternatively, an extract can be used which is obtained by extraction or steam distillation. Accordingly, the extract can be aqueous, ethanolic or aqueous-ethanolic. Depending on the concentration it is recommended to dilute the juice or extract with water, for example such that the amount of non-aqueous constituents is about 15 to 35, preferably about 20 to 25% by weight. To hold the anthocyanins and hydroxycinnamic acids in stable solution it is recommended to acidify the dilutions, for example, with formic acid, lactic acid or citric acid, adjusting them to a pH value in the range of about 2 to 4, preferably, about 3.

Subsequently, the acidified dilution is passed over an adsorber column which contains a resin which is selective for the hydroxycinnamic acids and polyphenols. It has shown that macroporous, crosslinked polystyrene resins not carrying other functional groups are suitable for this purpose. These are, in fact, not only specific for the anthocyanins or anthocyanidins, but they surprisingly concentrate the two hydroxycinnamic acids (a) and (b) in the synergistic ratio. Typical examples of suitable adsorber resins comprise the product Lewatit® VP OC 1064 MD PH, Amberlite XAD7 (Lanxess) or Symtrap® (Symrise). Desorption is performed using aqueous alcohol, specifically, aqueous ethanol.

Food and Dietary Supplements

A further subject matter of the invention relates to food or dietary supplements, either comprising antioxidant compositions, comprising
(a) caffeic acid,
(b) sinapinic acid and, optionally,
(c) polyphenols,
or
extracts, comprising
(a) caffeic acid,
(b) sinapinic acid and, optionally,
(c) polyphenols,
each with the proviso that components (a) and (b) are present in a weight ratio of about 85:15 to 98:2, preferably about 87:13 to 97:3.

As far as the products constitute food products to which the antioxidant compositions or extracts are directly added, they are, for example, baked products, for example, bread, dry biscuits, cake, other pastry, sweets (e.g. chocolates, chocolate bar products, other bar products, fruit gum, soft and hard caramels, chewing gum), alcoholic or non-alcoholic beverages (e.g. coffee, tea, iced tea, wine, wine-containing beverages, beer, beer-containing beverages, liqueurs, schnapps, brandies, (carbonated) fruit-containing lemonades, (carbonated) isotonic beverages, (carbonated) soft drinks, nectars, spritzers, fruit and vegetable juices, fruit or vegetable juice preparations, instant beverages (e.g. instant cocoa beverages, instant tea beverages, instant coffee beverages, instant fruit beverages), meat products (e.g. ham, fresh sausage preparations or raw sausage preparations, seasoned oder marinated fresh meat or salted meat products), eggs or egg products (dried whole egg, egg white, egg yolk), cereal products (e.g. breakfast cereals, muesli bars, pre-cooked instant rice products), dairy products (e.g. milk beverages, buttermilk beverages, yoghurt, kefir, cream cheese, soft cheese, hard cheese, dried milk powder, whey, whey beverages, butter, buttermilk, partly or wholly hydrolized products containing milk proteins), products from soy protein or other soy bean fractions (e.g. soy milk and products prepared thereof, beverages containing soy protein, preparations containing soy lecithine, fermented products such as tofu or tempe or products prepared thereof), products from other vegetable protein sources, for example, oat protein beverages, fruit preparations (e.g. jams, fruit ice cream, fruit sauces, fruit fillings), vegetable preparations (e.g. ketchup, sauces, dried vegetables, deep-freeze vegetables, pre-cooked vegetables, boiled vegetables), snack articles (e.g. baked or fried potato chips (crisps) or potato dough products, extrudates on the basis of maize or peanuts), products on the basis of fat and oil or emulsions thereof (e.g. mayonnaise, remoulade, dressings), other ready-made meals and soups (e.g. dry soups, instant soups, pre-cooked soups), seasonings and, particularly, sprinkle-on seasonings, which are used, for example, on snacks. The antioxidant compositions or extracts can particularly be used in sports drinks, particularly in such sports drinks intended for the regeneration of the athlete after intense training, or those which increase the athletes' performance capacity.

The compositions are usually added in amounts of about 0.1 bis 5, preferably, about 0.5 to 3 and more particularly about 1 to 2% by weight. The same amounts apply to the extracts; optionally, they refer to the content of active ingredients.

1. Capsules

If the products are dietary supplements, they are usually applied without further additives, excluding pure additives. In this case, macrocapsules or microcapsules are preferably used. Macrocapsules, preferably, consist of gelatin, or they are spray-dried products based on polysaccharides or dextrins. They usually have a particle diameter of about 0.5 to 1.5 cm. "Microcapsules" or "Nanocapsules" are understood by the expert to be spherical aggregates with a diameter of about 0.0001 to about 5 mm and preferably 0.005 to 0.5 mm, which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, molten waxes are absorbed in a matrix ("microsponge") which, as microparticles, may be additionally coated with film-forming polymers. According to a third process, particles are alternatingly coated with polyelectrolytes of different charges ("layer-by-layer" method). The microscopically small capsules can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers such as polyacrylate, polyamide, polyvinyl alcohol or polyvinyl pyrrolidone. Examples of state of the art microcapsules are the following commercial products (the membrane material is shown in brackets) Hallcrest Microcapsules (gelatin, gum arabic), Coletica Thalospheres (maritime collagen), Lipotec Millicapseln (alginic acid, agar agar), Induchem Unispheres (lactose, microcrystalline cellulose, hydroxypropylmethyl cellulose), Unicerin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids) as well as Primaspheres and Primasponges (chitosan, alginates) and Primasys (phospholipids).

2. Chewing Gums

A further form of administration of the anti-oxidative compositions can be in the form of chewing gums. These products typically contain a water-insoluble and a water-soluble component.

The water-insoluble base, which is also referred to as "gum base", typically comprises natural or synthetic elastomers, resins, fats and oils, plasticizers and softeners, fillers, dyes and optionally waxes. The base normally makes up 5 to 95% by weight, preferably 10 to 50% by weight, and more particularly 20 to 35% by weight of the composition as a whole. In one typical form of embodiment of the invention, the base is composed of between 20 and 60% by weight synthetic elastomers, 0 to 30% by weight natural elastomers, 5 to 55% by weight plasticizers, 4 to 35% by weight fillers, and in small amounts additives such as dyes, antioxidants and the like, with the proviso that they are water-soluble only in small amounts, if at all.

Suitable synthetic elastomers are, for example, polyisobutylenes with average molecular weights (as measured by GPC) of 10,000 to 100,000 and preferably 50,000 to 80,000, isobutylen/isoprene copolymers ("butyl elastomers"), styrene/butadiene copolymers (styrene:butadiene ratio, for example, 1:3 to 3:1), polyvinyl acetates with average molecular weights (as measured by GPC) of 2,000 to 90,000 and preferably 10,000 to 65,000, polyisoprenes, poly-ethylenes, vinyl acetate/vinyl laurate copolymers and mixtures thereof. Examples of suitable natural elastomers are rubbers such as, for example, smoked or liquid latex or guayuls, and natural gums, such as jelutong, lechi caspi, perillo, sorva, massaranduba balata, massaranduba chocolate, nispero, rosindinba, chicle, gutta hang kang and mixtures thereof. The choice of the synthetic and natural elastomers and their mixing ratios essentially depends on whether or not bubbles are to be produced with the chewing gums ("bubble gums"). Elastomer mixtures containing jelutong, chicle, sorva and massanduraba are preferably used.

In most cases, the elastomers are too hard or lack plasticity for satisfactory processing, so it has been found to be of advantage to use special plasticizers which, of course, must also satisfy, in particular, all requirements relating to their being allowed as food additives. In this respect, esters of resin acids are particularly suitable, for example, esters of lower aliphatic alcohols or polyols with wholly or partly hydrogenated, monomeric or oligomeric resin acids. In particular, the methyl, glycerol or pentaerythritol esters or mixtures thereof are used for this purpose. Alternatively, terpene resins, which can be derived from α-pinene, β-pinene, δ-limonene or mixtures thereof, can also be used.

Suitable fillers or texturizers are magnesium or calcium carbonate, ground pumice stone, silicates, especially magnesium or aluminium silicates, clays, aluminium oxides, talcum, titanium dioxide, mono-, di- and tricalcium phosphate and cellulose polymers.

Suitable emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Suitable colourants and whiteners are, for example, the FD and C types approved for use in foods, plant and fruit extracts and titanium dioxide.

The gum bases may contain waxes or be wax-free; examples of wax-free compositions can be found inter alia in U.S. Pat. No. 5,286,500, to the disclosure of which reference is herein specifically made.

In addition to the water-insoluble gum base, chewing gum preparations regularly comprise a water-soluble portion, consisting, for example, of softeners, sweeteners, fillers, flavourings, flavour enhancers, emulsifiers, colourants, acidifiers, antioxidants and the like, here with the proviso that the constituents are at least sufficiently water-soluble. Depending on the water-solubility of the particular representatives, individual constituents may thus be both part of the water-insoluble and the water-soluble phase. It is, however, also possible to use combinations of, for example, one water-soluble and one water-insoluble emulsifier, in which case the individual representatives are present in different phases. The water-insoluble component usually makes up 5 to 95% by weight and, preferably, 20 to 80% by weight of the composition.

Water-soluble softeners or plasticizers are added to the chewing gum compositions to improve chewability and the chewing feel and are present in the mixtures in quantities of typically 0.5 to 15% by weight. Typical examples are glycerol, lecithin and aqueous solutions of sorbitol, hydrogenated starch hydrolysates or corn syrup.

Suitable sweeteners are both sugar-containing or sugar-free compounds which are used in quantities of 5 to 95% by weight, preferably in quantities of 20 to 80% b weight and more particularly in quantities of 30 to 60% by weight, based on the chewing gum composition. Typical saccharide sweeteners are sucrose, dextrose, maltose, dextrin, dried invert sugar, fructose, fructose, levulose, galactose, corn syrup and mixtures thereof. Suitable sugar substitutes are sorbitol, mannitol, xylitol, hydrogenated strarch hydrolysates, maltitol and mixtures thereof. Further suitable additives are so-called high-intensity artificial sweeteners (HIAS) such as, for example, sucralose, aspartame, acesulfam salts, alitam, saccharin and saccharin salts, cyclamic acid and salts thereof, glycyrrhicins, dihydrochalcones, thaumatin, monellin and the like either individually or in the form of mixtures. The hydrophobic HIAS, which are the subject of International Patent Application WO 2002 091849 A1 (Wrigleys), are also particularly effective, as well as Stevia extracts and their active ingredients, particularly, Ribeaudioside A. The quantity in which these substances are used is primarily determined by their intensity and is typically in the range from 0.02 to 8% by weight.

Fillers are particularly suitable for the production of low-calorie chewing gums and may be selected, for example, from polydextrose, raftilose, rafitilin, fructo-oligosaccharides (Nutra-Flora), palatinose oligosaccharides, guar gum hydrolysates (Sun Fiber) and dextrins.

The choice in flavourings is virtually unlimited and is not critical to the essence of the invention. They normally make up 0.1 to 15% by weight and preferably 0.2 to 5% by weight of the chewing gum composition. Suitable flavourings are, for example, essential oils, synthetic aromas and the like, such as, for example, aniseed oil, Japanese anise oil, caraway oil, eucalyptus oil, fennel oil, citrus oil, wintergreen oil, clove oil and the like, such as used, for example, in oral and dental care products.

The chewing gums may further comprise auxiliaries and additives, which are suitable, for example, for dental care, more particularly for controlling plaque and gingivitis, such as, for example, chlorhexidine, CPC or triclosan. They may also contain pH adjusters (for example, buffers or urea), anti-caries agents (for example, phosphates or fluorides), biogenic agents (antibodies, enzymes, caffeine, plant extracts), providing these substances are permitted in foods and do not undesirably interact with one another.

Pharmaceutical Preparations

A further subject matter of the invention relates to pharmaceutical preparations for the protection of the human or animal body against antioxidant damage, either comprising antioxidant compositions, comprising
(a) caffeic acid,
(b) sinapinic acid and, optionally,
(c) polyphenols,
or
extracts, comprising
(a) caffeic acid,
(b) sinapinic acid and, optionally,
(c) polyphenols,
each with the proviso that components (a) and (b) are present in a weight ratio of about 85:15 to 98:2, preferably, about 87:13 to 97:3. If pharmaceutical compositions are meant, the same considerations will apply to them as described above to dietary supplements. It is a fact that these compositions will need to be considered as so-called "nutraceuticals" or "cosmeceuticals" and are therefore located in an area where pharmaceutics, nutrition and cosmetics overlap. If the compositions are ingested orally, it is in this context also referred to as a "beauty from inside" effect, because in doing so it is attempted to prevent the skin from ageing.

Cosmetic Means

A further subject matter of the invention relates to cosmetic means, either comprising antioxidant compositions, comprising
(a) caffeic acid,
(b) sinapinic acid and, optionally,
(c) polyphenols,
or
extracts, comprising
(a) caffeic acid,
(b) sinapinic acid and, optionally,
(c) polyphenols,
each with the proviso that components (a) and (b) are present in a weight ratio of about 85:15 to 98:2, preferably, about 87:13 to 97:3.

The cosmetic means of the invention may comprise further typical additives and auxiliaries such as, for example, mild surfactants, oil components, emulsifiers, pearlizing waxes, consistency factors, thickeners, superfatting agents, stabilizers, polymers, silicon compounds, fats, waxes, lecithins, phospholipids, UV protection fatcors, humectants, biogenic agents, antioxidants, deodorants, antitranspirants, anti-dandruff agents, film formers, swelling agents, insect repellants, self-tanning agents, tyrosin inhibitors (depigmentation agents), hydrotropes, solubilizers, preservatives, perfume oils, colourants and the like. As many pharaceutical compositions include similar constituents, the following examples are also applicable.

1. Surfactants

Anionic, non-ionic, cationic and/or amphoteric or zwitterionic surfactants can be comprised as surface-active substances, the portion of which in the means is usually from about 1 to 70, preferably, from 5 to 50 and, particularly, from 10 to 30% by weight. Typical examples of anionic surfactants are soaps, alkyl benzenesulfonates, alkanesulfonates, olefin sulfonates, alkylther sulfonates, glycerol ether sulfonates, α-methyl ester sulfonates, sulfofatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partly oxidized alk(en)yl oligoglycosides or glucoronic acid derivatives, fatty acid-N-alkyl glucamides, protein hydrolyzates (more particularly wheat-based plant products) polyol fatty acid esters, sugar esters, sorbitan esters, and amine oxides. If the anionic surfactants contain polyglycol ether chains, they may have a conventional homolog distribution although they preferably have a narrow-range homolog distribution. Typical examples of cationic surfactants are quaternary ammonium compounds such as, for example, dimethyl distearyl ammonium chloride, and esterquats, more particularly quaternized fatty acid trialkanolamine ester salts. Typical examples of amphoteric or zwitterionic surfactants are alkyl betaines, alkyl-amido-betaines, amino-propionates, amino-glycinates, imidazolinium-betaines and sulfo-betaines. All surfactants mentioned are known compounds. Typical examples of particularly suitable mild, i.e. particularly skin-compatible surfactants are fatty alcohol polyglycol ether sulfates, monoglyceride sulphate, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, the latter, preferably, wheat-based proteins.

2. Oil Components

Suitable oil components are, for example, Guerbet alcohols based on fatty alcohols containing 6 to 18 and preferably 8 to 10 carbon atoms, esters of linear C6-22 fatty acids with linear or branched C6-22 fatty alcohols or esters of branched C6-13 carboxylic acids with linear or branched, C6-22 fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear C6-22 fatty acids with branched alcohols, more particularly 2-ethyl hexanol, esters of C18-38 alkylhydroxycarboxylic acids with linear or branched C6-22 fatty alcohols, more particularly Dioctyl Malate, esters of linear and/or branched fatty acids with polyhydric alcohols (for example propylene glycol, dimer diol or trimer triol) and/or Guerbet alcohols, triglycerides of C6-C10 fatty acids, liquid mono-, di-, trig- lyceride mixtures of C6-C18 fatty acids, esters of C6-22 fatty alcohols and/or Guerbet alcohols with aromatic carboxylic acids, more particularly benzoic acid, esters of C2-12 dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched C6-C22-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched C6-C22-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), (ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

3. Emulsifiers

Suitable emulsifiers are, for example, nonionic surfactants from at least one of the following groups:

products of the addition of 2 to 30 mol ethylene oxide and/or 0 to 5 mol propylene oxide onto linear C8-22 fatty alcohols, onto C12-22 fatty acids, onto alkyl phenols containing 8 to 15 carbon atoms in the alkyl group and onto alkylamines containing 8 to 22 carbon atoms in the alkyl group;

alkyl and/or alkenyl oligoglycosides containing 8 to 22 carbon atoms in the alk(en)yl group and ethoxylated analogs thereof;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5.000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol and/or mixed esters of fatty acids containing 6 to 22 carbon atoms, methyl glucose and polyols, preferably glycerol or polyglycerol.

mono-, di- and trialkyl phosphates and mono-, di- and/or tri-PEG-alkyl phosphates and salts thereof;

wool wax alcohols;

polysiloxane/polyalkyl/polyether copolymers and corresponding derivatives;

block copolymers, for example, polyethylene glycol-30 Dipolyhydroxystearate;

polymer emulsifiers, for example Pemulen types (TR-1, TR-2) of Goodrich or Cosmedia® SP of BASF Personal Care and Nutrition GmbH;

polyalkylene glycols and glycerol carbonate.

Particularly suitable emulsifiers are explained below in more detail:

(i) Alkoxylates.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. C12/18 fatty acid monoesters and diesters of addition products of ethylene oxide onto glycerol are known as lipid layer enhancers for cosmetic formulation.

(ii) Alkyl and/or Alkenyl Oligoglycosides.

Alkyl and/or alkenyl oligoglycosides, their production and their use are known from the prior art. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

(iii) Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide onto the partial glycerides mentioned are also suitable.

(iv) Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(v) Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide).

(vi) Anionic Emulsifiers.

Typical anionic emulsifiers are aliphatic fatty acids containing 12 to 22 carbon atoms such as, for example, palmitic acid, stearic acid or behenic acid and dicarboxylic acids containing 12 to 22 carbon atoms such as, for example, azelaic acid or sebacic acid.

(vii) Amphoteric and Cationic Emulsifiers.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a C8/18 alkyl or acyl group, contain at least one free amino group and at least one —COOH— or —SO3H-group in the molecule and which are capable of forming inner salts. Examples of suitable ampholytic surfactants are N-alkyl glycines, N-alkyl propionic acids, N-alkylamino-butyric acids, N-alkyliminodipropionic acids, N-hydroxyethyl-N-alkylamidopropyl glycines, N-alkyl taurines, N-alkyl sarcosines, 2-alkylaminopropionic acids and alkylamino-acetic acids containing around 8 to 18 carbon atoms in the alkyl group. Particularly preferred ampholytic surfactants are N-cocoalkylaminopropionate, cocoacylaminoethyl aminopropionate and C12/18 acyl sarcosine. Finally, cationic surfactants are also suitable emulsifiers, those of the esterquat type, preferably methyl-quaternized difatty acid triethanolamine ester salts, being particularly preferred.

4. Fats and Waxes

Typical examples of fats are glycerides, i.e. solid or liquid, vegetable or animal products which consist essentially of mixed glycerol esters of higher fatty acids, suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

5. Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

6. Cooling Agents

Cooling agents are compounds which create a sensation of cold on the skin. These are usually menthol compounds which—in addition to the basic structure Menthol—are, for example, selected from the group consisting of Menthol Methyl Ether, Menthone Glyceryl Acetal (FEMA GRAS[1] 3807), Menthone Glyceryl Ketal (FEMA GRAS 3808), Menthyl Lactate (FEMA GRAS 3748), Menthol Ethylene Glycol Carbonate (FEMA GRAS 3805), Menthol Propylene Glycol Carbonate (FEMA GRAS 3806), Menthyl-N-ethyloxamat, Monomethyl Succinate (FEMA GRAS 3810), Monomenthyl Glutamate (FEMA GRAS 4006), Menthoxy-1,2-propanediol (FEMA GRAS 3784), Menthoxy-2-methyl-1,2-propandiol (FEMA GRAS 3849) and the menthanecarboxylic acid esters and -amides WS-3, WS-4, WS-5, WS-12, WS-14 and WS-30 the mixtures thereof.

[1] FEMA stands for "Flavor and Extracts Manufacturers Association", and GRAS is defined as "Generally Regarded As Safe". A FFMA GRAS denomination means that the substance marked as such has been tested according to standard methods and is considered toxicologically safe.

A first significant representative of these substances is Monomenthyl Succinate (FEMA GRAS 3810). Both the succinate and the analogous Monomenthyl Glutarate (FEMA GRAS 4006) are important representative of monomenthyl esters of di- and polycarboxylic acids:

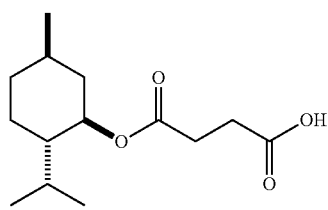

-continued

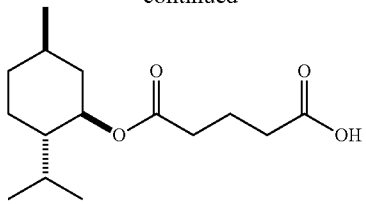

Examples of uses of these substances are found, for example, in publications WO 2003 043431 (Unilever) or EP 1332772 A1 (IFF).

The next important group of preferred menthol compounds within the meaning of the invention comprises carbonate esters of menthol and polyols such as, for example, glycolene, glycerol or carbohydrates such as, for example, Menthol Ethylenglycol Carbonate (FEMA GRAS 3805=Frescolat® MGC), Menthol Propylenglycol Carbonate (FEMA GRAS 3784=Frescolat® MPC), Menthol 2-Methyl-1,2-propandiol Carbonate (FEMA GRAS 3849) or the corresponding sugar derivatives. Also preferred are the menthol compounds Menthyl Lactate (FEMA GRAS 3748=Frescolat® ML) and, particularly, Menthone Glyceryl Acetal (FEMA GRAS 3807) or Menthone Glyceryl Ketal (FEMA GRAS 3808), which is marketed under the trade name Frescolat® MGA. Particularly preferable among these substances are Menthone Glyceryl Acetal/Ketal and Menthyl Lactate as well as Menthol Ethylene Glycol Carbonate or Menthol Propylene Glycol Carbonatw which are marketed by the applicant under the trade names Frescolat® MGA, Frescolat® ML, Frescolat® MGC and Frescolat® MPC.

Menthol compounds, which have a C—C bond in the 3-position were developed for the first time in the 1970ies. Of these, also a number of representatives within the meaning of the invention may be used. These substances are generally referred to as WS types. A menthol derivative forms the base body, in which the hydroxyl group is replaced by a carboxyl group (WS-1). All other WS types are derived from this structure WS, such as, for example, the preferred species within the meaning of the invention WS-3, WS-4, WS-5, WS-12, WS-14 and WS-30.

7. Consistency Factors and Thickeners

Suitable consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for exampie, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

8. Superfatting Agents and Stabilizers

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Metal salts of fatty acids such as, for example, magnesium, aluminium and/or zinc stearate or ricinoleate may be used as stabilizers.

9. Polymers

Suitable cationic polymers are, for example, cationic cellulose derivatives such as, for exampie, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

10. Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

11. UV Protection Factors

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV protection factors are usually present in amounts of 0.1 to 5 and preferably of 0.2 to 1% by weight. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomethyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone or Dioctyl Butamido Triazone (Uvasorb® HEB);

propane-1,3-diones such as, for example, 1-(4-tert.butylphenyl)-3-(4'-methoxyphenyl)-propane-1,3-dione);

ketotricyclo(5.2.1.0)decane derivatives.

Suitable water-soluble substances are:

2-phenylbenzimidazole-5-sulfonic acid and alkali metal, alkaline earth metal, ammonium, alkylammonium, alkanolammonium and glucammonium salts thereof;

1H-Benzimidazole-4,6-Disulfonic Acid, 2,2'-(1,4-Phenylene)Bis-, Disodium Salt (Neo Heliopan® AP)

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789), 2-(4-Diethylamino-2-hydroxybenzoyl)-benzoic acid hexylester (Uvinul® A Plus), 1-phenyl-3-(4'-isopropylphenyl)-propane-1,3-dione and enamine compounds. The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000, Eusolex® T, Eusolex® T-ECO, Eusolex® T-S, Eusolex® T-Aqua, Eusolex® T-45D (all by Merck), Uvinul $TiO_2$ (BASF). Suitable hydrophobic coating materials are, above all, silicones and, among these, especially trialkoxyoctylsilanes or simethicones. So-called micro- or nanopigments are preferably used in sun protection products. Micronized zinc oxide such as, for example, Z-COTE® or Z-COTE HP1® is preferably used.

12. Humectants

Humectants contribute towards improving the sensory properties of the composition and serves to regulate the skin moisture level. In addition, it can contribute towards improving the cold stability of the compositions according to the invention, particularly when emulsions are concerned. The humectants are normally present in a quantity of 0.1 to 15% by weight, preferably 1 to 10% by weight and more particularly 5 to 10% by weight. According to the invention, suitable humectants are inter alia amino acids, pyrrolidone carboxylic acid, lactic acid and salts thereof lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof, ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol, triglycerol and butylenglycol.

13. Biogenic Agents and Antioxidants

Biogenic agents are, for example, tocopherol, tocopherol acetate, tocopherol palmitate, ascorbic acid, (desoxy)ribonucleic acid and fragmentation products thereof, β-glucans, retinol, bisabolol, allantoin, phytantriol, panthenol, AHA acids, amino acids, ceramides, pseudo-ceramides, essential oils, plant extracts, for example prunus extract, bambara nut extract, and vitamin complexes.

Antioxidants interrupt the photo-chemical reaction chain which is triggered as soon as UV radiation penetrates the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propyl-thiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and heptathionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nor-dihydroguaiac resin acid, nordihydroguaiaretic acid, trihydroxybutyrophenone, uric acid and derivatives thereof, mannose and derivatives thereof, superoxide dismutase, zinc and derivatives thereof (for example ZnO, ZnSO4), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

14. Hydrotropes

In addition, hydrotropes, for example ethanol, isopropyl alcohol or polyols, may be used to improve flow behaviour; these substances mostly correspond to the carriers stated above. Suitable polyols preferably contain 2 to 15 carbon atoms and at least two hydroxyl groups. The polyols may contain other functional groups, more especially amino groups, or may be modified with nitrogen.

Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

15. Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetik-verordnung ("Cosmetics Directive").

16. Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, *cardamon, costus*, iris, calmus), woods (pinewood, sandalwood, guaiac wood, cedarwood, rosewood), herbs and grasses (tarragon, lemon grass, sage, thyme), needles and branches (spruce, fir, pine, dwarf pine), and resins and balsams (galbanum, elemi, benzoin, myrrh, olibanum, opoponax). Also suitable are animal products, such as, for example, civet and castoreum. Typical synthetic fragrance compounds are products of the ester, ether, aldehyde, ketone, alcohol, and hydrocarbon type. Examples of perfume compounds of the ester type are benzyl acetate, phenoxyethyl isobutyrate p-tert.butyl cyclohexylacetate, linalyl acetate, dimethyl benzyl carbinyl acetate, phenyl ethyl acetate, linalyl benzoate, benzyl formate, ethyl methyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal, the ketones include the ionones, α-isomethyl ionone and methyl cedryl ketone, the alcohols include anethol, citronellol, eugenol, isoeugenol, geraniol, linalool, phenylethyl alcohol and terpineol, the hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components, for example, sage oil, camomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, ⍺-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, γ-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

17. Dyes

Suitable dyes are any of the substances suitable and approved for cosmetic purposes, as compiled, for example, in the publication "Kosmetische Firbemittel" ("Cosmetic Dyes") by the Farbstoffkommission der Deutschen Forschungsgesellschaft (The Dyes Commission of the German Research Association), Verlag Chemie, Weinheim, 1984, pp. 81-106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The total portion of additives and auxiliaries can be from 1 to 50, preferably from 5 to 40% by weight—based on the means. The means can be produced by conventional cold or hot processes; preferably, the phase inversion temperature method is applied.

INDUSTRIAL APPLICATION

Further subject matters of the present invention comprise:
A first method to improve the oxidative stability of foods, wherein an effective amount of the antioxidant composition or an extract comprising it is added to them;
A second non-therapeutic method to protect the human or animal body against oxidative damages, wherein it is treated with an effective amount of the antioxidant composition or with an extract comprising it.
A third method to improve the oxidative stability of foods, wherein an effective amount of the antioxidant composition or an extract comprising it is added to them.
A first use of a mixture, comprising
(a) caffeic acid,
(b) sinapinic acid and, optionally,
(c) anthocyanins,
with the proviso that components (a) and (b) are present as an antioxidant in a weight ratio of about 85:15 to about 98:2.
A further use of an extract, comprising
(a) caffeic acid,
(b) sinapinic acid and, optionally,
(c) anthocyanins,
with the proviso that components (a) and (b) are present as an antioxidant in a weight ratio of about 85:15 to about 98:2.

It is understood that the advantageous forms of embodiments mentioned above in context with the compositions, the extracts and the means containing them also apply to the methods and uses according to the invention. Insofar a repetition is deemed unnecessary.

EXAMPLES

Examples 1a and 1b

Preparation of an Extract of Sour Cherry

A concentrate of sour cherry juice was diluted with water to obtain a non-aqueous portion of 20% by weight and adjusted to a pH value of about 3 using 0.1% by weight hydrochloric acid to hold the anthocyanins in stable solution. The solution was passed to an adsorber column, which was filled with an adsorber resin (example 1a: Lewatit® VP OC1064, Lanxess AG, example 1b: Amberlite XAD 7). In contrast to other ion exchanger resins said column material is characterized in that both very polar and very unpolar compounds are removed. In doing so, surprisingly, a concentration of particularly the hydroxycinnamic acids in the indicated weight ratio and the anthocyanins was observed. Desorption was then performed using acidified aqueous ethanol. Subsequently, the eluate was dehydrated, for example, by lyophilisation, belt drying or spray-drying. Table 1 indicates the composition of the extract.

TABLE 1

Components of the extract (amounts in ppm)

| Components | 1a | 1b |
|---|---|---|
| Anthocyanins or anthocyanidins (total)* | 98.410 | 65.056 |
| Ferulic acid | <1 | 10 |
| Gallic acid | <1 | 15 |
| Caffeic acid | 80 | 650 |
| Ellagic acid | 50 | 1.200 |
| p-Coumaric acid | 70 | 120 |
| Chlorogenic acid | 2800 | 13.800 |
| Sinapinic acid | 5 | 20 |
| Maltose | n/s | 900 |
| Weight ratio caffeic acid:sinapinic acid | | 97:3 |

*calculated as cyanidin-3-o-glucoside

Examples 2 to 4, comparison examples V1 to V3

Determination of the Antioxidant Effect

The antioxidant effect and the synergy between the individual components were determined according to the OARC-fluorescein method, in which inhibition time and the inhibition degree are reflected in a measured value. The measurements were performed by means of the device Synergy H4 by BioTek Inc., the calculated values were taken from a calibration curve with Trolox used as a standard. The method is described in more detail, for example, in the publications by Prior et. al., J. Agric Food. Chem. 50, pp. 4437-4444 (2000) and Dovalos et. al, ibid 52, pp. 58-54 (2004). These publications are incorporated into this patent application by reference with regard to the description of the measuring method. The results are summarized in Table 2 and shown in FIG. 1.

TABLE 2

Measured and calculated ORAC values

| Example | Caffeic acid | Sinapinic acid | Measured | Calculated | Δ | Δ [%] |
|---|---|---|---|---|---|---|
| V1 | 100 parts by weight | — | 21.587 | — | — | — |
| V2 | — | 100 parts by weight | 11.459 | — | — | — |
| V3 | 50 parts by weight | 50 parts by weight | 16.627 | 16.523 | 104 | 0.62 |
| 2 | 97 parts by weight | 3 parts by weight | 22.245 | 21.284 | 961 | 4.52 |
| 3 | 93 parts by weight | 7 parts by weight | 21.757 | 20.863 | 894 | 4.29 |
| 4 | 87 parts by weight | 13 parts by weight | 21.578 | 20.321 | 1.258 | 6.19 |

The positive difference determined between the calculated and the measured ORAC values shows that these mixtures act synergistically by increasing the oxidative effect. With a value of 4 to 6% this deviation is also significant.

Examples 5 to 7, Comparison Example V4

Effectiveness Against Free Radicals

The effectiveness of the tested substances against free radicals was chemically and biochemically tested according to various methods:

Method A

In a first method, diphenylpicrylhydrazyl (DPPH°) was used, which is a relatively stable radical which yields a purple-coloured solution. The optical density (OD) was determined at 513 nm.

Method B

Hydroxyl radicals were released from hydrogen peroxide in the presence of iron(II) ions and EDTA and used for the oxidation of desoxyribose. The oxidation product forms a pink compound in combination with thiobarbituric acid. The concentration thereof corresponds with the optical density at 532 nm. It was tested whether less desoxyribose would oxidize in the presence of the test products, i.e. whether a smaller amount of free radicals is released.

Method C

The test described above was carried out in the absence of EDTA to check the suitability of the test substances to form iron complexes.

Method D

Xanthine oxidase is an enzyme which is released as a result of oxidative stress, catabolizing the reduction of the purine bases adenine and guanine into uronic acid and superoxide anions. The latter ones dismutate spontaneously or in the presence of superoxide dismutase into hydrogen peroxide and oxygen. The amount of superoxide anions can be determined by NBT reduction by means of their optical density at 490 nm. It was tested whether less superoxide anions are generated in the presence of the text substances, or whether more anions are destroyed.

Sour cherry extracts with a standardized anthocyanin content and a content of caffeic and sinapinic acid of 700 ppm were used. The extracts, however, differed in their weight ratio in which both acids were present. The results are summarized in Table 3.

TABLE 3

Effectiveness against free radicals (A indicated as optical density units, other indications given in %-rel.)

| | | | Test method | | | |
|---|---|---|---|---|---|---|
| Example | Caffeic acid | Sinapinic acid | A | B | C | D |
| V4 | 50 parts by weight | 50 parts by weight | 0.0013 | 0.26 | 0.9 | 0.59 |
| 4 | 97 parts by weight | 3 parts by weight | 0.0019 | 0.23 | 0.9 | 0.54 |
| 5 | 93 parts by weight | 7 parts by weight | 0.0023 | 0.22 | 0.8 | 0.53 |
| 7 | 87 parts by weight | 13 parts by weight | 0.0026 | 0.21 | 0.8 | 0.52 |

The results allow the conclusion that the test substances have an antioxidant effect which is clearly above of the one provided by an extract of a mixture of caffeic acid and sinapinic acid in a ratio of 1:1. When EDTA is absent, the test substances show a particularly high hydroxyl ion quenching potential, which shows that they form stable iron complexes. Finally they possess a strong potential to prevent the formation of superoxide anions.

The invention is in the following further explained by means of numerous formulation examples without being limited to them.

TABLE I

Soft drinks (amounts as % by weight)

| Components | A | B | C | D | E | F | G |
|---|---|---|---|---|---|---|---|
| Sucrose | 10 | 10 | 7 | — | — | 8 | 7 |
| Glucose/Fructose Syrup | — | — | — | — | 10 | — | — |
| Rebaudioside A 95% | — | — | 0.02 | 0.05 | — | — | — |
| Citric acid | 0.15 | 0.15 | 0.06 | 0.15 | 0.15 | 0.15 | 0.15 |
| Phosphoric acid | — | — | 0.07 | — | — | — | — |
| Colouring caramel | — | — | 0.14 | — | — | — | — |
| Caffeine | — | — | 0.01 | — | — | — | — |
| Lemon flavouring | 0.1 | 0.05 | — | 0.1 | 0.1 | 0.1 | 0.1 |
| Lime flavouring | — | 0.05 | — | — | — | — | — |
| Beverage emulsion type "Cola" | — | — | 0.05 | — | — | — | — |
| Phloretin | — | — | 0.002 | 0.003 | — | 0.002 | 0.001 |
| Hesperetin | — | — | 0.001 | 0.002 | — | — | 0.002 |
| Sour cherry extract according to example 1 | 0.1 | 0.1 | 0.1 | 0.1 | 0.1 | 0.1 | 0.1 |
| Homoeriodictyol sodium salt | — | — | 0.005 | 0.005 | — | — | — |
| Water | Fill up to 100 | | | | | | |

The components were mixed in the order indicated and filled up to 100% with water. The mixtures were filled into glass bottles and carbonated.

TABLE II

Hard caramels (amounts in % by weight)

| Components | A | B | C | D |
|---|---|---|---|---|
| Sugar | 74.50 | — | — | — |
| Palatinit, Type M | — | 74.00 | 75.50 | 75.00 |
| Citric acid | 0.5 | 1.0 | 0.5 | — |
| Dye, yellow | — | 0.01 | — | — |
| Dye, red | — | — | 0.01 | — |
| Dye, blue | 0.01 | — | — | 0.01 |
| Peppermint flavouring | 0.1 | — | — | 0.1 |
| Lemon flavouring | — | 0.1 | — | — |
| Red berries flavouring | — | — | 0.1 | — |
| Rebaudioside A 98% | — | 0.040 | — | 0.040 |
| Balansin A | — | 0.005 | 0.010 | 0.005 |
| Hesperetin | — | 0.001 | — | 0.001 |
| Phloretin | — | 0.002 | — | — |
| Sour cherry extract according to example 1 | 0.02 | 0.01 | 0.02 | 0.02 |
| Water | Fill up to 100 | Fill up to 100 | Fill up to 100 | Fill up to 100 |

TABLE III

Low-fat yoghurt (amounts in % by weight)

| Components | A | B | C | D |
|---|---|---|---|---|
| Sucrose | 10 | 8 | 6 | — |
| Rebaudioside A 98% | — | — | — | 0.050 |
| Sour cherry extract according to example 1 | 0.2 | 0.1 | 0.2 | 0.2 |
| Hesperetin | — | 0.001 | 0.001 | 0.002 |
| Phloretin | — | — | 0.002 | 0.002 |
| Homoeriodictyol sodium salt | — | — | — | 0.005 |
| Yoghurt, 0.1% fat | Fill up to 100% | | | |

TABLE IV

Fruit gum (amounts in % by weight)

| Components | A | B |
|---|---|---|
| Saccharose | 34.50 | 8.20 |
| Glucose syrup, DE 40 | 31.89 | 30.09 |
| Iso Sirup C* Tru Sweet 01750 (Cerestar GmbH) | 1.50 | 2.10 |
| Gelatine 240 Bloom | 8.20 | 9.40 |
| Polydextrose (Litesse ® Ultra, Danisco Cultor GmbH) | — | 24.40 |
| Dye | 0.01 | 0.01 |
| Lemon flavouring | 0.20 | — |
| Cherry flavouring | — | 0.10 |
| Sour cherry extract according to example 1 | 0.2 | 0.1 |
| Water | Fill up to 100 | Fill up to 100 |

TABLE V

Sugar-free chewing gum (amounts in % by weight)

| Components | content |
|---|---|
| Gum base | 30.00 |
| Sorbitol powder | Fill up to 1.00 |
| Palatinit | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70%. in water | 14.00 |
| Glycerol | 1.00 |
| Peppermint flavouring | 1.50 |
| Sour cherry extract according to example 1 | 0.20 |

TABLE VI

Sun protection composition (fill up to 100% by weight with water and preservative)

| Composition (INCI) | A | B | C | D | E | F | G | H | I | J |
|---|---|---|---|---|---|---|---|---|---|---|
| Dehymuls ® PGPH Polyglyceryl-2 Dipolyhydroxystearte | 4.0 | 3.0 | — | 5.0 | — | — | — | — | — | — |
| Lameform ® TGI Polyglyceryl-3 Diisostearate | 2.0 | 1.0 | — | — | — | — | — | — | — | — |

TABLE VI-continued

Sun protection composition (fill up to 100% by weight with water and preservative)

| Composition (INCI) | A | B | C | D | E | F | G | H | I | J |
|---|---|---|---|---|---|---|---|---|---|---|
| Emulgade ® PL 68/50<br>Cetearyl Glucoside (and) Cetearyl Alcohol | — | — | — | — | 4.0 | — | — | — | 3.0 | — |
| Eumulgin ®82<br>Ceteareth-20 | — | — | — | — | — | — | — | 2.0 | — | — |
| Tegocare ® PS<br>Polyglyceryl-3 Methylglucose Distearate | — | — | 30 | — | — | — | 4.0 | — | — | — |
| Eumulgin VL 75<br>Polyglyceryl-2 Dipolyhydroxystearate (and) Lauryl Glucoside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS<br>Glyceryl Stearate | — | — | — | — | — | 2.0 | 4.0 | — | — | 4.0 |
| Lanette ® O<br>Cetearyl Alcohol | — | — | 2.0 | — | 2.0 | 4.0 | 2.0 | 4.0 | 4.0 | 1.0 |
| Antaron ® V 216<br>PVP/Hexadecene Copolymer | — | — | — | — | — | 3.0 | — | — | — | 2.0 |
| Myritol ® 818<br>Cocoglycerides | 5.0 | — | 10.0 | — | 8.0 | 6.0 | 6.0 | — | 5.0 | 5.0 |
| Finsolv ® TN<br>C12/15 Alkyl Benzoate | — | 6.0 | — | 2.0 | — | — | 3.0 | — | — | 2.0 |
| Cetiol ® J 600<br>Oleyl Erucate | 7.0 | 4.0 | 3.0 | 5.0 | 4.0 | 3.0 | 3.0 | — | 5.0 | 4.0 |
| Cetiol ® OE<br>Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL<br>Hexadecanol (and) Hexyldecyl Laurate | — | 7.0 | 3.0 | 7.0 | 4.0 | — | — | — | 1.0 | — |
| Bisabolol | 1.2 | 1.2 | 1.2 | 1.2 | 1.2 | 1.2 | 1.2 | 1.2 | 1.2 | 1.2 |
| Sour cherry extract according to example 1 | 0.2 | 0.2 | 0.2 | 0.2 | 0.2 | 0.2 | 0.2 | 0.2 | 0.2 | 0.2 |
| Hydagen ® CMF<br>Chitosan | 1.0 | 1.0 | 1.0 | 1.0 | 1.0 | 1.0 | 1.0 | 1.0 | 1.0 | 1.0 |
| Copherol ® F 1300<br>Tocopherol/Tocopheyl Acetate | 0.5 | 1.0 | 1.0 | 2.0 | 1.0 | 1.0 | 1.0 | 2.0 | 0.5 | 2.0 |
| Neo Heliopan ® Hydro<br>Sodium Phenylbenzimidazole Sulfonate | 3.0 | — | — | 3.0 | — | — | 2.0 | — | 2.0 | — |
| Neo Heliopan ® 303<br>Octocrylene | — | 5.0 | — | — | — | 4.0 | 5.0 | — | — | 10.0 |
| Neo Hellopan ® 8B<br>Benzophenone-3 | 1.5 | — | — | 2.0 | 1.5 | — | — | — | 2.0 | — |
| Neo Heliopan ® E 1000<br>Isoamyl p-Methoxycinnamate | 5.0 | — | 4.0 | — | 2.0 | 2.0 | 4.0 | 10.0 | — | — |
| Neo Heliopan ® AV<br>Octyl Methoxycinnamate | 4.0 | — | 4.0 | 3.0 | 2.0 | 3.0 | 4.0 | — | 10.0 | 2.0 |
| Uvinul ® T 150<br>Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | — | 5.0 | — | — |
| Glycerol (86% by weight) | 5.0 | 5.0 | 5.0 | 5.0 | 5.0 | 5.0 | 5.0 | 5.0 | 5.0 | 5.0 |

The invention claimed is:

1. An antioxidant composition, comprising
   (a) caffeic acid,
   (b) sinapinic acid and, optionally,
   (c) polyphenols,
   with the proviso that components (a) and (b) are present in a weight ratio of about 85:15 to 98:2.

2. The composition of claim 1, wherein it contains components (a+b) and (c) in a weight ratio of about 5:95 to about 1:99.

3. An extract, comprising
   (a) caffeic acid,
   (b) sinapinic acid and, optionally,
   (c) polyphenols,
   with the proviso that components (a) and (b) are present in a weight ratio of about 85:15 to 98:2.

4. The extract of claim 3, wherein it comprises
   (a) 150 to 1.000 ppm caffeic acid,
   (b) 10 to 50 ppm sinapinic acid, and
   (c) 10 to 60% by weight polyphenols, and
   is essentially filled up to 100% by weight with solvents.

5. The extract of claim 3, wherein has a total content of hydroxycinnamic acids of about 0.5 to about 3% by weight.

6. The extract of claim 3, wherein is obtained from plants or fruits selected from the group consisting of Açai (*Euterpe oleracea*); Aronia (e.g. *Aronia arbutifolia, Aronia melanocarpa; Aronia prunifolia*); black currants and red currants (e.g. *Ribes rubrum, Ribes spciatum, Ribes alpinum, Ribes schlechtendalii, Ribes multiflorum, Ribes petraeurn, Ribes trite, Ribes nigrum*); blackberries (*Rubus* sp.); black carrots (*Daucus carota*); black tomatoes (*Solarium lycopersicum*); blood oranges (*Citrus sinensis*); blueberries (*Vaccinium corymbosum, Vaccinium angustifolium*); black haw (*Prunus spinosa*); bilberries (*Vaccinium ulginosum*); cloudberries (*Rubus chamaemorous*); lingonberries (e.g. *Vaccinium oxycoccos, Vaccinium microcarpus, Vaccinium macrocarpus, Vaccinium erythrocarpus*); black crowberries (e.g. *Empetrum nigrum, Empetrum eamesil, Empetrum rumbrum, Empetrum hermaphroditum*); elderberries (e.g. *Sambucus nigra, Sambucus racemase*); hibiscus (*Hibiscus sabdariffa, Roselle*); cowberries (e.g. *Vaccinium vitas idaea*); Magellan barberries ("Calafate"), *Berberis microphylla, Breberis buxifolia*);

Maqui berries (e.g. *Aristotelia chilensis*) mountain huckleberries (*Vaccinium membranaceum*); plums and damsons (*Prunus domestica*); raspberries (*Rufous idaeus, Rubus occidentalis*); red gooseberries (*Ribes uva-crispa, Ribes grossularia*); red grapes (*Vitis vinifera, Vitis labrusca, Vitis riparia, Vitis rotundifolia*); rowanberries (*Sorbus aucparia*); sour cherries (*Prunus avium, Prunus cerasus*); strawberries (*Fragaria ananassa*); sweet cherries (*Prunus avium*); tay berries (*Rubus* X).

7. The extract of claim 3, wherein it has
   (a) an ORAC value of above 5,000 and/or
   (b) a polyphenol content of above 40% by weight and/or
   (c) an anthocyanine content of about 6 to about 25% by weight and/or
   (d) an ash content of less than 3% by weight and/or
   (e) a sugar content of less than 0.25% by weight.

8. A method of production of the extract of claim 3, wherein
   (i) a juice or an extract is produced from the plants or fruits, which is then acidified,
   (ii) the acidified product is passed over an adsorber column which contains as adsorption means a macroporous, crosslinked, non-functionalized polystyrene resin,
   (iii) the mixture comprising components (a), (b) and (c) is desorbed by means of aqueous alcohol and finally
   (iv) the eluate is dried.

9. A food or a dietary supplement, comprising the composition of claim 1.

10. A pharmaceutical composition for the protection of the human or animal body against oxidative damage, comprising the composition of claim 1.

11. A cosmetic means, comprising the composition of claim 1.

12. A method to improve the oxidative stability of food, wherein an effective amount of a composition of claim 1 is added to the food.

13. A non-therapeutic method for the protection of the human or animal body against oxidative damage, wherein said body is treated with an effective amount of a composition of claim 1.

14. A food or a dietary supplement, comprising the extract of claim 2.

15. A pharmaceutical composition for the protection of the human or animal body against oxidative damage, comprising the extract of claim 2.

16. A cosmetic means, comprising the extract of claim 2.

17. A method to improve the oxidative stability of food, wherein an effective amount of an extract of claim 2 is added to the food.

18. A non-therapeutic method for the protection of the human or animal body against oxidative damage, wherein said body is treated with an effective amount of an extract of claim 2.

\* \* \* \* \*